United States Patent
Wölk et al.

(10) Patent No.: US 8,796,173 B2
(45) Date of Patent: Aug. 5, 2014

(54) METHOD FOR PRODUCING A CATALYST ARRANGEMENT FOR THE PRODUCTION OF PHTHALIC ANHYDRIDE

(75) Inventors: Hans-Jörg Wölk, Rosenheim (DE); Gerhard Mestl, München (DE)

(73) Assignee: Süd-Chemie IP GmbH & Co. KG, Munich (DE)

( * ) Notice: Subject to any disclaimer, the term of this patent is extended or adjusted under 35 U.S.C. 154(b) by 31 days.

(21) Appl. No.: 13/496,967

(22) PCT Filed: Sep. 8, 2010

(86) PCT No.: PCT/EP2010/005510
§ 371 (c)(1),
(2), (4) Date: Jun. 13, 2012

(87) PCT Pub. No.: WO2011/032658
PCT Pub. Date: Mar. 24, 2011

(65) Prior Publication Data
US 2012/0245365 A1    Sep. 27, 2012

(30) Foreign Application Priority Data
Sep. 17, 2009   (DE) .......................... 10 2009 041 960

(51) Int. Cl.
| B01J 31/00 | (2006.01) |
| B01J 27/00 | (2006.01) |
| B01J 27/198 | (2006.01) |
| B01J 23/00 | (2006.01) |
| C07D 307/89 | (2006.01) |

(52) U.S. Cl.
USPC ........... 502/350; 502/102; 502/208; 502/209; 502/349; 549/248; 549/249

(58) Field of Classification Search
USPC ................. 502/102, 208, 209, 349, 350, 353; 549/248, 249
See application file for complete search history.

(56) References Cited

U.S. PATENT DOCUMENTS

| 2,035,606 | A | 3/1936 | Jaeger |
| 3,684,741 | A | 8/1972 | Friedrichsen et al. |
| 3,799,886 | A | 3/1974 | Felice et al. |
| 4,203,906 | A | 5/1980 | Takada et al. |
| 5,677,261 | A | 10/1997 | Tenten et al. |
| 5,792,719 | A | 8/1998 | Eberle et al. |
| 5,969,160 | A | 10/1999 | Lindström |
| 6,288,273 | B1 | 9/2001 | Heidemann et al. |
| 6,458,970 | B1 | 10/2002 | Hefele et al. |
| 6,700,000 | B1 | 3/2004 | Heidemann et al. |
| 6,774,246 | B2 | 8/2004 | Reuter et al. |
| 7,371,893 | B2 | 5/2008 | Storck et al. |
| 7,390,911 | B2 | 6/2008 | Neto et al. |
| 7,592,293 | B2 | 9/2009 | Guckel et al. |
| 7,592,294 | B2 | 9/2009 | Storck et al. |
| 7,615,513 | B2 | 11/2009 | Guckel et al. |
| 7,985,705 | B2 | 7/2011 | Storck et al. |
| 8,067,618 | B2 | 11/2011 | Lautensack et al. |
| 2009/0318712 | A1 * | 12/2009 | Wilmer et al. ................ 549/231 |
| 2010/0210857 | A1 | 8/2010 | Storck et al. |

FOREIGN PATENT DOCUMENTS

| DE | 1 280 756 | 10/1968 |
| DE | 1 642 938 | 5/1971 |
| DE | 2005 969 | 8/1971 |
| DE | 1 769 998 | 2/1972 |
| DE | 2 106 796 A1 | 8/1972 |
| DE | 2 159 441 | 6/1973 |
| DE | 28 30 765 A1 | 1/1980 |
| DE | 198 07 018 A1 | 8/1998 |
| DE | 197 09 589 A1 | 9/1998 |
| DE | 198 28 583 A1 | 1/1999 |
| DE | 100 40 827 A1 | 3/2002 |
| DE | 103 23 461 A1 | 12/2004 |
| DE | 103 23 817 A1 | 12/2004 |
| DE | 103 23 818 A1 | 12/2004 |
| DE | 103 44 846 A1 | 4/2005 |
| DE | 10 2004 026 472 | 12/2005 |
| EP | 0 714 700 A2 | 6/1996 |
| EP | 0 744 214 A1 | 11/1996 |
| EP | 0 964 744 B1 | 12/1999 |
| EP | 1 084 115 B1 | 3/2001 |
| WO | WO 98/37967 | 9/1998 |
| WO | WO 99/61433 | 12/1999 |
| WO | WO 2004/103561 A1 | 12/2004 |
| WO | WO 2006/092304 A1 | 9/2006 |
| WO | WO 2006/092305 A1 | 9/2006 |
| WO | WO2006092304 | * 9/2006 |
| WO | WO 2007/125096 A1 | 11/2007 |
| WO | WO 2007/147733 A1 | 12/2007 |
| WO | WO 2009/095216 A2 | 8/2009 |

OTHER PUBLICATIONS

Towae et al., "Phthatic acid and Derivatives" *Ullmann's Encyclopedia of Industrial Chemistry*, vol. A20, 1992, pp. 181-211.
Brunauer et al., "J.Am. Chem. Soc", vol. 60:309-19 (1938).
International Search Report PCT/EP2010/005510 dated Nov. 23, 2010.

* cited by examiner

*Primary Examiner* — T. Victor Oh
(74) *Attorney, Agent, or Firm* — RatnerPrestia

(57) ABSTRACT

A method for producing phthalic anhydride by catalytic gas-phase oxidation of o-xylene and/or naphthalene, carried out by means of a catalyst arrangement which has a first catalyst layer at the gas inlet side and at least one second catalyst layer after the first catalyst layer in the gas flow direction with different catalytic activity, wherein when the gas-phase oxidation is being carried out a lower maximum temperature is formed in the first catalyst layer than in the second catalyst layer. Furthermore, a method for producing the catalyst arrangement, as well as the catalyst arrangement itself.

54 Claims, No Drawings

METHOD FOR PRODUCING A CATALYST ARRANGEMENT FOR THE PRODUCTION OF PHTHALIC ANHYDRIDE

CROSS-REFERENCE TO RELATED APPLICATION

This application is a U.S. National Stage application, claiming benefit under 35 U.S.C. §§120 and 365 of International Application No. PCT/EP2010/005510, filed Sep. 8, 2010, and claiming benefit under 35 U.S.C. §119 of German Application No. 10 2009 041 960.8, filed Sep. 17, 2009, the entire disclosures of both prior applications being incorporated herein by reference in their entirety.

BACKGROUND

The invention relates to a method for producing phthalic anhydride by catalytic gas-phase oxidation of o-xylene and/or naphthalene, wherein the method is carried out by means of a catalyst arrangement which has a first catalyst layer at the gas inlet side and at least one second catalyst layer after the first catalyst layer in the gas flow direction with different catalytic activity, characterized in that when the gas-phase oxidation is being carried out a lower maximum temperature is formed in the first catalyst layer than in the second catalyst layer. The invention furthermore relates to a method for producing the catalyst arrangement according to aspects of the invention, as well as the catalyst arrangement itself according to aspects of the invention.

The industrial-scale production of phthalic anhydride is achieved by the catalytic gas-phase oxidation of o-xylene and/or naphthalene. For this purpose, a catalyst suitable for the reaction is placed in a reactor, preferably a so-called multitube fixed-bed reactor, in which a plurality of tubes are arranged in parallel, and a mixture of the hydrocarbon(s) and an oxygen-containing gas, for example air, is passed through it from top to bottom. Because of the strong heat generation of such oxidation reactions, it is necessary to flush heat-carrier medium around the reaction tubes in order to prevent so-called hotspots and thus to remove the heat energy that has formed. This energy can be used for the production of steam. As a rule, a salt melt, and here preferably a eutectic mixture of $NaNO_2$ and $KNO_3$, is used as heat-carrier medium.

Today, multilayer catalyst beds are used for the oxidation of o-xylene and/or naphthalene to phthalic anhydride. The aim of this is to adjust the activity of the individual catalyst layers to the course of reaction along the reaction axis. It is thereby possible to achieve a high yield of the valuable product PSA and, at the same time, as low as possible a yield of undesired intermediate products such as e.g. maleic anhydride and/or phthalide. Usually, the first catalyst layer (=the catalyst layer placed closest to the reactor inlet) has the lowest activity, as the highest concentration of educts and thus the highest reaction rate occur in the area close to the reactor inlet. Heat being released during the chemical conversion heats the reaction gas up to the point at which the energy generated by the reaction is exactly as great as the energy emitted to the coolant. This hottest point in the reaction tube is called the "hotspot". Too high an activity in the first catalyst layer will lead to an uncontrolled increase in the hotspot temperature, which can usually lead to a reduction in selectivity or even to a "runaway".

A further important aspect that must be borne in mind in the design of the activity of the individual catalyst layers is the position of the hotspot in the first catalyst layer. As the catalyst activity reduces as the operating time increases, the position of the hotspot shifts ever further towards the reactor outlet. This can even go so far that the hotspot migrates from the first catalyst layer into the second catalyst layer or even into a layer even further on. Because of the associated significantly reduced PSA yield, in such a case the catalyst needs to be exchanged frequently, which leads to high losses in output.

EP 1 084 115 B1 describes a multilayer catalyst arrangement for the oxidation of o-xylene and/or naphthalene to phthalic anhydride in which the activity of the individual catalyst layers increases continuously from the reactor inlet side to the reactor outlet side. This is achieved by increasing the active material, combined with lowering the alkali metal content of the catalyst such that the catalyst layer directly at the catalyst inlet has the lowest active material content and the highest alkali metal content.

DE 103 23 818 A1 describes a multilayer catalyst arrangement for the oxidation of o-xylene and/or naphthalene to phthalic anhydride, made of at least three successive catalyst layers in which the activity of the individual catalyst layers increases continuously from the reactor inlet side to the reactor outlet side. This is achieved by using $TiO_2$ with different BET surface areas such that the BET surface area of the $TiO_2$ used is smaller in the catalyst layer at the reactor inlet than in the following catalyst layers and is at its largest in the last catalyst layer (reactor outlet).

DE 103 23 461 A1 describes a multilayer catalyst arrangement for the oxidation of o-xylene and/or naphthalene to phthalic anhydride in which the activity of the individual catalyst layers increases from the reactor inlet side to the reactor outlet side, wherein the ratio of $V_2O_5$ to $Sb_2O_3$ in the first catalyst layer is between 3.5:1 and 5:1.

DE 103 23 817 A1 describes a multilayer catalyst arrangement for the oxidation of o-xylene and/or naphthalene to phthalic anhydride, made of at least three successive catalyst layers in which the activity of the individual catalyst layers increases continuously from the reactor inlet side to the reactor outlet side, wherein the last layer, lying closest to the reactor outlet, contains more than 10 wt.-% $V_2O_5$ and has phosphorus as the only layer.

A disadvantage of the catalysts or multilayer catalyst systems according to the invention indicated there is that, despite the use of such structured catalysts, the life of the catalyst is not satisfactory, in particular with regard to the increasing shift of the hotspot in the direction of the gas flow. A positioning of the hotspot in the most active catalyst layer further towards the gas outlet side also limits the possibility of finely adjusting the selectivity of the catalyst to reduce undesired by-products.

SUMMARY

There is therefore a continued need for improved multilayer catalyst arrangements for producing phthalic anhydride or other products obtainable by partial oxidation of hydrocarbons.

An object according to aspects of the present invention was therefore to provide a catalyst arrangement, in particular for producing phthalic anhydride by gas-phase oxidation of o-xylene and/or naphthalene, which avoids the disadvantages of the state of the art and in particular makes possible an advantageous positioning of the hotspot and a longer life of the catalysts contained in the catalyst arrangement. This is to be associated with an increase in the product yield.

This object is achieved by a method for producing/optimizing a catalyst arrangement for the gas-phase oxidation of hydrocarbons comprising the arrangement of a first catalyst layer of length $L_1$ and at least one second catalyst layer of length $L_2$, each with different catalytic activities with respect to the gas-phase oxidation of hydrocarbons, wherein the first catalyst layer is arranged at the gas inlet side for a reaction gas and the at least one second catalyst layer is arranged following the first catalyst layer in the gas flow direction, characterized in that the catalyst arrangement has a temperature profile during the gas-phase oxidation of hydrocarbons which increases from the first catalyst layer to the second.

This object is also achieved by a catalyst arrangement for the gas-phase oxidation of hydrocarbons comprising a first catalyst layer $K_1$ of length $L_1$ and at least one second catalyst layer $K_2$ of length $L_2$, each with different catalytic activities with respect to the gas-phase oxidation of hydrocarbons, wherein the first catalyst layer $K_1$ and the at least one second catalyst layer $K_2$ together form a catalyst layer K with the total length $L_1+L_2$ and wherein the first catalyst layer $K_1$ is arranged at the gas inlet side for a reaction gas and the second catalyst layer $K_2$ is arranged after the first catalyst layer $K_1$ in the gas flow direction, characterized in that the catalyst arrangement has a temperature profile which increases during the gas-phase oxidation of hydrocarbons from the first catalyst layer to the second.

A further subject according to aspects of the invention is a method for producing phthalic anhydride by catalytic gas-phase oxidation of o-xylene and/or naphthalene, wherein the method is carried out by means of a catalyst arrangement which has a first catalyst layer at the gas inlet side and at least one second catalyst layer after the first catalyst layer in the gas flow direction with different catalytic activities, characterized in that when the gas-phase oxidation is being carried out a lower maximum temperature (hotspot temperature) is formed in the first catalyst layer than in the second catalyst layer.

Preferred embodiments of the invention can be found in the dependent claims.

DESCRIPTION

According to aspects of the invention, it is preferred that a catalyst layer with a higher catalytic activity than the second catalyst layer is used as first catalyst layer. It is preferred that the temperature profile is such that during the gas-phase oxidation of hydrocarbons the maximum temperature in the first catalyst layer is 10 to 100° C., more preferably 20 to 90° C., most preferably 30 to 70° C., lower than in the second catalyst layer.

According to an embodiment, it is preferred that a third catalyst layer is arranged after the second catalyst layer in the gas flow direction, wherein the catalytic activity increases from the second catalyst layer to the third catalyst layer. The temperature profile preferably decreases from the second catalyst layer to the third. In particular, the temperature profile is such that during the gas-phase oxidation of hydrocarbons the maximum temperature in the third catalyst layer is 10 to 100° C., more preferably 20 to 90° C., most preferably 30 to 70° C., lower than in the second catalyst layer.

According to a further embodiment of the invention, it is preferred that a fourth catalyst layer is arranged after the third catalyst layer in the gas flow direction, wherein the catalytic activity increases from the third catalyst layer to the fourth catalyst layer. The temperature profile preferably decreases from the second catalyst layer to the fourth (and also to the third). In particular, the temperature profile is such that during the gas-phase oxidation of hydrocarbons the maximum temperature in the fourth catalyst layer is 10 to 100° C., more preferably 20 to 90° C., most preferably 30 to 70° C., lower than in the second catalyst layer and 1 to 50° C., more preferably 5-25° C., most preferably 5 to 10° C. lower than in the third catalyst layer.

In addition, further catalyst layers can be arranged afterwards in the gas flow direction, wherein their catalytic activity preferably increases further. Furthermore, it is preferred that the maximum temperature during the gas-phase oxidation of hydrocarbons is also lower than in the second catalyst layer. The maximum temperature can also decrease overall from layer to layer, starting from the second layer with the highest maximum temperature.

According to aspects of the invention, it was surprisingly found that, when, starting from a catalyst arrangement according to the state of the art which has at least one, preferably two or more catalyst layers, a part of the first catalyst layer placed towards the gas inlet side is replaced by an upstream layer of a catalyst with a higher activity than that of the first catalyst layer of the starting configuration according to the state of the art, this is advantageous for the positioning and stabilization of the temperature maximum. In this procedure, the remaining part of the first catalyst layer of the starting configuration becomes the second catalyst layer in the catalyst arrangement according to aspects of the invention. Due to the upstream catalyst layer located directly at the reactor inlet with a higher activity than that of the following second catalyst layer (corresponding to the first catalyst layer in the starting configuration), the reaction rate is clearly increased in a comparatively short area at the reactor inlet in which, because of the low temperature, only low reaction rates and thus low chemical conversion rates usually occur. The result of this in the catalyst arrangement according to aspects of the invention is an earlier positioning of the temperature maximum (hotspot) closer to the reactor inlet than without the upstream first catalyst layer according to the state of the art. This is advantageous with regard to a long life (service life), as described above, and also makes possible a better fine adjustment of the catalyst selectivity in the catalyst sections that are located towards the gas outlet side behind the above-named hotspot. Yield and selectivity can thereby also be increased.

Within the meaning of this invention, an upstream or following catalyst layer is most often referred to, wherein here the arrangement of the catalyst layer always means the gas flow direction in the catalyst arrangement. A following catalyst layer thus means following the previous catalyst layer in the gas flow direction.

The length of the upstream catalyst layer as well as the activity of the upstream catalyst layer are primarily dependent on the position of the hotspot, i.e. of the temperature maximum, during the conversion of hydrocarbons in a gas-phase oxidation. The hotspot can thus be determined in a starting catalyst arrangement suitable for the desired purpose. This position of the hotspot in the starting configuration, expressed as the distance of the hotspot in the first catalyst layer from the start of the catalyst bed (at the gas inlet side of a reactor), can be called $A_{HS}$ and in many catalyst arrangements of the state of the art is between 60 and 120 cm, in particular between 70 and 100 cm. According to aspects of the invention, such a part of the first catalyst layer of the starting configuration is now preferably replaced, wherein the length of this replaced catalyst layer is shorter than the distance $A_{HS}$ (measured from the start of the catalyst layer at the gas inlet side to the hotspot) which was determined for the starting configuration. It is thereby to be avoided that in the catalyst arrangement according to the invention the hotspot lies in the more active, upstream catalyst layer. According to aspects of the invention, the hotspot, i.e. the maximum temperature, accordingly preferably lies in the second catalyst layer of the catalyst arrangement according to aspects of the invention. It was surprisingly found that by using the upstream, more active catalyst layer a reduction in the distance $A_{HS}$ can be achieved, i.e. the hotspot lies closer towards the gas inlet side than in the starting configuration. The associated improvement in the life and the performance of the catalyst has already been mentioned here.

According to an embodiment of the invention, it is preferred that the length $L_1$ of the first catalyst layer is 0.1 to 0.9 times $A_{HS}$, wherein $A_{HS}$ means the position of a hotspot (HS) which develops during a gas-phase oxidation of hydrocarbons in a catalyst layer $K_A$, corresponding to the second catalyst layer, with the length $L$ (=$L_1$+$L_2$), wherein the position of the hotspot is measured in the gas flow direction from the start at the gas inlet side of the catalyst layer $K_A$ to the hotspot. The catalyst layer $K_A$ thus corresponds to a first catalyst layer of any suitable starting configuration. In this catalyst layer, the position $A_{HS}$ of the hotspot is determined accordingly and the position can be used to specify the length of the desired first (upstream) catalyst layer for the catalyst arrangement according to the invention.

As already indicated above, any catalyst arrangement having at least one, preferably at least two catalyst layers described in the state of the art for the partial oxidation of hydrogens, in particular for producing phthalic anhydride by gas-phase oxidation of o-xylene and/or naphthalene, can thus be used as starting configuration. For example, reference can be made here to the catalyst arrangements disclosed in DE 10 2004 026 472 or in the above-named EP 1 084 115 A1, DE 103 23 818 A1, DE 102 23 461 A1, DE 103 23 817 A1. Likewise, other catalyst arrangements having at least one, preferably at least two different catalyst layers familiar to a person skilled in the art from the state of the art can also be used as starting configuration for producing the catalyst arrangement according to aspects of the invention. In the two-layer or multilayer PSA catalyst arrangements of the state of the art, as a rule it is provided that the catalyst activity increases from layer to layer from the gas inlet side to the gas outlet side. Accordingly, the hotspot is to be positioned in the first, least active catalyst layer which, at the same time, has a high selectivity.

According to aspects of the invention, it is preferred that the catalyst layers have different compositions, wherein the catalyst layers, in particular the first (upstream) and the second catalyst layers of the catalyst arrangement according to the invention, can differ, for example only by a different active material content, for example also in relation to a specific reactor volume.

As already stated above, the length of the catalyst layer, in addition to the activity of the upstream first catalyst layer, is important for the positioning of the temperature maximum. According to aspects of the invention, it is preferred that the ratio of the length of the first catalyst layer to the second catalyst layer is less than or equal to 0.9, preferably 0.1 to 0.9, in particular 0.1 to 0.7 and particularly preferably between 0.15 and 0.5. It is thereby ensured that the first layer is not too long compared with the second layer in which the temperature maximum is preferably to be located.

According to a further aspect of the invention, it is preferred that approximately 5 to 60% of the total length L of the catalyst layer K consists of the first catalyst layer. Particularly preferably, approximately 10 to 50% of the catalyst layer K, calculated from the start of the catalyst bed at the gas inlet side, consists of the first catalyst layer.

According to a further embodiment of the invention, it is preferred that the catalyst comprises at least one third catalyst layer which is arranged following the second catalyst layer in the gas flow direction. In addition, further catalyst layers, for example a fourth, fifth, sixth, seventh or eighth catalyst layer, and so on, can be arranged afterwards.

Within the meaning of aspects of the invention, it is preferred that the length of the first catalyst layer is approximately 5 to 30%, particularly preferably 10 to 25%, of the length of all catalyst layers, relative to the total length of the catalyst arrangement in the gas flow direction.

In addition to other factors, the level of the axial temperature gradient in the surrounding cooling medium also plays a role in configuring the length. In any case, the length of the first catalyst layer is shorter than would correspond to the position of a notional hotspot, measured as the distance from the start of the catalyst bed until the maximum temperature is reached, which would form if, instead of the first catalyst layer, the corresponding area were also filled with catalyst of the second layer (corresponding to the catalyst of the first layer of the starting configuration).

According to an embodiment of the invention, it is preferred that the catalytic activity increases starting from the second catalyst layer to the third and optionally further following catalyst layers. Generally, the expressions first (upstream), second, third or fourth catalyst layer, unless otherwise indicated, are based on the catalyst arrangement according to the invention and are used in connection with the present invention as follows. The catalyst layer of the catalyst arrangement according to the invention placed towards the gas inlet side is called the first or upstream catalyst layer. Towards the gas outlet side, the catalyst arrangement according to the invention preferably contains another at least two further catalyst layers which are called the second, third or optionally fourth catalyst layer. The third catalyst layer lies closer to the gas outlet side than the second catalyst layer. The individual catalyst layers can be arranged with or without thorough mixing in the boundary areas in order to obtain the multilayer catalyst arrangement according to the invention.

According to a further preferred embodiment, the activity of the third catalyst layer is higher than that of the second catalyst layer in the catalyst arrangement according to the invention. Also preferably, the activity of an optional fourth catalyst layer is higher than that of the third catalyst layer in the catalyst arrangement according to the invention. If a fifth catalyst layer is present, the activity of the fifth catalyst layer is again preferably higher than the activity of the fourth catalyst layer. It was furthermore found that it is particularly advantageous for the performance and life of the catalyst if the activity increases from the second layer towards the outlet side of the reaction mixture, i.e. towards the last catalyst layer continuously, i.e. from catalyst layer to catalyst layer in the catalyst arrangement according to aspects of the invention.

According to aspects of the invention, the activity of the first catalyst layer can be set by all measures familiar to a person skilled in the art such that it is higher than the activity of the following second catalyst layer. Within the meaning of aspects of the invention, it is accordingly preferred that the different catalytic activity in the respective catalyst layers is conditional on different chemical and/or physical properties of the catalysts contained in the respective catalyst layers.

By physical properties of the catalysts can be meant for example the geometric shape of the catalyst body, which for example influences the bulk density of the catalyst in a reactor tube or the surface area or the back pressure. By chemical properties can be meant for example compositions of and presence of various promoters in the catalysts and the like.

For example, the increased activity in the first catalyst layer can be achieved by a higher level of active material than in the second layer, by a larger BET surface area of a support oxide for the catalytically active material than in the second layer, by a higher level of catalytically active compound, for example vanadium and/or antimony, than in the second layer, by a lower alkali metal content, e.g. caesium, than in the second layer, by an increase in the bulk density in the first catalyst layer, for example by using a different geometry or ring geometry of the shaped body used, by the presence or a larger quantity of other activity-increasing promoters than in the second catalyst layer, or by the absence or a smaller quantity of activity-limiting promoters than in the second catalyst layer, as well as combinations of two or more of the named measures.

Within the meaning of aspects of this invention, it is particularly preferred that the first catalyst layer has a higher active material content and/or a larger BET surface area compared with the second catalyst layer. As the BET surface area of the catalyst layer primarily depends on the BET surface area of the support oxide used, according to a preferred embodiment the BET surface area of the support oxide in the first catalyst layer is larger than the BET surface area of the support oxide in the second catalyst layer.

The above measures for setting an increased activity of the first catalyst layer compared with the second catalyst layer can of course also be used for the preferred adjustment of the activities of the following catalyst layers, for example the third and fourth, fifth catalyst layers, etc.

According to a preferred embodiment of the invention, the activity of the upstream catalyst layer is at least 5%, in particular at least 10%, preferably at least 20%, in particular preferably at least 30%, higher than the activity of the following second catalyst layer. A method for determining or comparing the activity of catalyst layers is indicated below in the method part. In addition, the activity of the first layer in an embodiment of the invention is at most 300% higher than that of the first catalyst layer, preferably at most 200%, more preferably at most 100% and in particular preferably at most 80% higher than the activity of the second layer. Particularly good results are achieved if the activity of the first catalyst layer lies in the range of from 10 to 30% higher than that of the second catalyst layer.

Preferably, the composition of the second and following catalyst layers of the starting configuration can remain unchanged. Preferably, the layer length of the third and optionally following catalyst layers of the starting catalyst arrangement (i.e. without upstream first catalyst layer) can also remain unchanged.

In particular preferably, the second catalyst layer is the least active catalyst layer in the whole catalyst arrangement according to the invention.

According to aspects of the invention, the length of the first catalyst layer is preferably measured such that under the desired reaction conditions the hotspot occurs in the second catalyst layer and not in the first catalyst layer itself. For this reason, a preferred length of the first catalyst layer in the catalyst arrangement according to aspects of the invention is 20-70 cm, particularly preferably 30-60 cm. The usual length of reactor tubes into which for example the catalyst arrangement according to aspects of the invention is introduced is between approximately 2.5 and 3.5 m. In addition to the volumetric flow rate and the charge, the axial temperature gradient in the surrounding cooling medium (salt bath) in particular also influences the length of the first catalyst layer. With a high axial temperature gradient which develops in the case of poor coolant circulation, the temperature of the coolant is up to 10° C. higher at the reactor inlet than at the reactor outlet. In this case, the length of the upstream catalyst length is to be chosen shorter and its activity more moderate than in the case of a low axial temperature gradient in the coolant.

The catalysts used according to aspects of the invention in the catalyst layers preferably comprise an inert support and a catalytically active material arranged thereon. The catalytically active material particularly preferably comprises a titanium-containing support oxide and, arranged thereon, preferably in layers, a catalytically active composition.

The catalytically active composition, or the catalytically active material, preferably contains as active component vanadium, niobium, antimony, boron, calcium, caesium, potassium, lithium, sodium, cobalt, iron, molybdenum, zirconium, rubidium, silver, thallium, bismuth, tungsten, tin, phosphorus and/or compounds and/or combinations thereof. Particularly preferably, the catalytically active material contains as active component vanadium, particularly preferably in the form of $V_2O_5$ and in addition also caesium and/or antimony, particularly preferably in the form of $Sb_2O_3$. Also preferably, phosphorus is contained in the catalytically active composition.

The titanium-containing support oxide preferably has a BET surface area of from 10 to 50 $m^2/g$, particularly preferably 15 to 45 $m^2/g$ and in particular approximately 20 to 35 $m^2/g$.

In a particularly preferred embodiment, the individual catalysts of the catalyst layers each contain at least titanium and preferably also vanadium in the catalytically active material. It was also found that particularly good results are achieved in the PSA production if the vanadium content of the catalytically active material in the first catalyst layer, calculated as $V_2O_5$, is more than 4 wt.-%, in particular more than 5 wt.-%. Further preferably, in each case caesium and/or antimony are also contained in the catalyst layers. According to a particularly preferred embodiment, at least the second catalyst layer has caesium, wherein the first catalyst layer preferably has a lower caesium content, or no caesium at all. It was found that the interaction of the upstream catalyst layer with a desired reaction rate for the primary conversion of o-xylene and/or naphthalene, immediately at the start of the catalyst arrangement on the gas inlet side, and the second catalyst layer with an earlier positioning of the hotspot closer to the reactor inlet can thereby be accomplished particularly well.

In a further preferred embodiment, the individual catalyst layers preferably have no molybdenum and/or no tungsten, in particular not in an atomic ratio to vanadium in the range of between 0.01 and 2. According to a further preferred embodiment, furthermore no nickel or cobalt is used in the catalysts used. According to yet another embodiment, the sodium content in the active material is preferably less than 500 ppm, in particular less than 450 ppm.

In a particularly preferred embodiment, the catalysts comprise the following ranges in the catalytically active material: $V_2O_5$ in the range of from 1 to 25 wt.-%, preferably 4 to 20 wt.-%, $Sb_2O_3$ in the range of from 0-4 wt.-%, preferably 0.5 to 3.5 wt.-%, caesium in the range of from 0-1 wt.-%, preferably 0.1 to 0.8 wt.-%, phosphorus in the range of from 0-2 wt.-%, preferably 0.2 to 1.5 wt.-%, in each case relative to the total weight of the catalytically active material. The proportion of the catalytically active material in the whole catalyst is preferably 4 to 20 wt.-%, more preferably 4 to 15 wt.-%.

In addition to the above components, at least 90 wt.-%, preferably at least 95 wt.-%, further preferably at least 98 wt.-%, in particular at least 99 wt.-%, further preferably 99.5 wt.-%, in particular 100 wt.-% of the rest of the active material consists of $TiO_2$.

Within the framework of the present invention, it was also found that particularly advantageous catalyst arrangements can be produced if the active material content decreases from the second catalyst layer to the catalyst layer placed towards the gas outlet side. According to an associated embodiment, the second catalyst layer has an active material content of between approximately 6 and 12 wt.-%, in particular between 6 and 11 wt.-%, the third catalyst layer has an active material content of between approximately 5 and 11 wt.-%, in particular between approximately 6 and 10 wt.-% and the fourth catalyst layer (if present) has an active material content of between approximately 4 and 10 wt.-%, in particular between approximately 5 and 9 wt.-%. However, in principle, catalysts are also included in which the active material content stays the same or increases from the second layer to the last layer, i.e.: active material content of $2^{nd}$ layer≤active material content of $3^{rd}$ layer≤ . . . ≤active material content of last layer.

According to another advantageous embodiment, at least the active material content of the last layer is higher than that of the second layer.

According to a particularly preferred embodiment, the catalyst according to the invention in the first catalyst layer has an active material content of between approximately 6 and 20 wt.-%, preferably between approximately 7 and 5 wt.-%.

According to a particularly preferred embodiment, the catalyst according to aspects of the invention has four catalyst layers. In this case, the fourth catalyst layer lies at the gas outlet side. The presence of additional catalyst layers downstream in the flow of gas, however, is not ruled out. For example, according to an embodiment according to aspects of the invention the fourth catalyst layer as defined herein can also be followed by a fifth catalyst layer. Irrespective of this, the use of a so-called finishing reactor in the production of phthalic acid is optionally also possible, such as described e.g. in DE-A-198 07 018 or DE-A-20 05 969.

According to a further preferred embodiment, the BET surface area of the $TiO_2$ used increases from the second catalyst layer to the catalyst layer placed towards the gas outlet side. In other words, it is preferred that the BET surface area of the $TiO_2$ used in the second catalyst layer is smaller than the BET surface area of the $TiO_2$ used in the (last) catalyst layer placed towards the gas outlet side. Preferred ranges for the BET surface area of the $TiO_2$ are 15 to 25 $m^2/g$ for the central catalyst layers, and 15 to 45 $m^2/g$ for the (last) catalyst layer placed towards the gas outlet side. Particularly advantageous catalysts are also obtained if the BET surface areas of the $TiO_2$ of the central catalyst layers are equal, while the BET surface area of the $TiO_2$ in the last catalyst layer is larger by comparison.

The BET surface area of the $TiO_2$ of the first catalyst layer is preferably larger than or equal to the BET surface area of the $TiO_2$ of the second or the central catalyst layers and in particular lies in the range of from approximately 15 to 45 $m^2/g$. According to an embodiment according to the invention, the BET surface area of the $TiO_2$ used is as follows: BET-$TiO_2$ of $2^{nd}$ layer≤BET-$TiO_2$ of $3^{rd}$ layer≤ . . . ≤BET-$TiO_2$ of last layer. BET-$TiO_2$ of $1^{st}$ layer≥BET-$TiO_2$ of $2^{nd}$ layer is still further preferred.

The temperature management during the gas-phase oxidation of o-xylene to phthalic anhydride is sufficiently known to a person skilled in the art from the state of the art, wherein reference can be made for example to DE 100 40 827 A1.

In general, when the catalyst according to aspects of the invention is used to produce phthalic anhydride, a mixture of a molecular oxygen-containing gas, for example air, and the starting material to be oxidized (in particular o-xylene and/or naphthalene) is passed through a fixed-bed reactor, in particular a multitube fixed-bed reactor which can consist of a plurality of tubes arranged in parallel. In the reactor tubes, there is in each case a bed made of at least one catalyst. The advantages of a bed made of several (different) catalyst layers have already been covered above. The catalyst arrangement according to the invention can thus be understood as a multilayer catalyst bed in a reactor tube. The catalyst arrangement forms a catalyst bed, preferably a fixed bed.

When the catalysts according to the invention are used to produce phthalic anhydride by gas-phase oxidation of o-xylene and/or naphthalene, it was surprisingly established that very good PSA yields are achieved with the catalyst arrangement according to the invention with very small proportions of phthalide and a position of the hotspot close to the reactor inlet, whereby an improved service life of the catalyst arrangement is made possible.

According to a preferred embodiment according to the invention, the $TiO_2$ used, which is usually used in the anatase form, has a BET surface area of at least 15 $m^2/g$, preferably between 15 $m^2/g$ and 60 $m^2/g$, in particular between approximately 15 $m^2/g$ and 45 $m^2/g$ and particularly preferably between 15 $m^2/g$ and 40 $m^2/g$. Furthermore, it is preferred that at least 30%, in particular at least 40% and up to 80%, preferably up to 75%, in particular up to 70% of the total pore volume of the $TiO_2$ is formed by pores with a radius of between 60 and 400 nm. Unless otherwise indicated, the determination of the pore volumes or pore proportions indicated here is carried out by means of mercury porosimetry (according to DIN 66133). The indication of the total pore volume relates in the present description in each case to the total pore volume measured by means of mercury porosimetry of between 7500 and 3.7 nm pore radius size.

Pores with a radius of more than 400 nm preferably represent less than approximately 30%, in particular less than approximately 22%, particularly preferably less than 20% of the total pore volume of the $TiO_2$ used.

Furthermore, it is preferred that approximately 50 to 75%, in particular approximately 50 to 70%, particularly preferably 50 to 65% of the total pore volume of the $TiO_2$ is formed by pores with a radius of from 60 to 400 nm, and preferably approximately 15 to 25% of the total pore volume by pores with a radius of more than 400 nm.

With respect to the smaller pore radii, it is preferred that less than 30%, in particular less than 20%, of the total pore volume of the $TiO_2$ is formed by pores with a radius of from 3.7 to 600 nm. A particularly preferred range here for this pore size is approximately 10 to 30% of the total pore volume, in particular 12 to 20%.

According to a further preferred embodiment, the $TiO_2$ used has the following particle size distribution: the $D_{10}$ value is preferably 0.5 µm or less, the $D_{50}$ value (i.e. the value at which half of the particles have a larger or smaller particle diameter respectively) is preferably 1.5 µm or less; the $D_{90}$ value is preferably 4 µm or less. Preferably, the $D_{90}$ value of the $TiO_2$ used is between approximately 0.5 and 20 µm, in particular between approximately 1 and 10 µm, particularly preferably between approximately 2 and 5 µm.

In electron microscope images, the $TiO_2$ used according to the invention preferably has an open-pored, spongy structure, wherein more than 30%, in particular more than 50%, of primary particles or crystallites are combined to form open-pored agglomerates. It is assumed that particularly favourable reaction conditions for the gas-phase oxidation are created by this particular structure of the $TiO_2$ used, which is reflected in the pore radius distribution.

In principle, in the catalyst according to the invention another titanium oxide with a specification other than that described above, i.e. a different BET surface area, porosimetry and/or particle size distribution, can also be used. According to aspects of the invention, it is particularly preferred that at least 50%, in particular at least 75%, particularly preferably the whole of the TiO$_2$ used, has a BET surface area and porosimetry as defined herein, and preferably also the described particle size distribution. Blends of different TiO$_2$ materials can also be used.

Depending on the envisaged use of the catalyst according to aspects of the invention, in addition to TiO$_2$, the usual components familiar to a person skilled in the art can be contained in the active material of the catalyst. The shape of the catalyst or its homogeneous or heterogeneous structure is also in principle not limited within the meaning of the present invention and can comprise any embodiment that is familiar to a person skilled in the art and appears to be suitable for the respective field of use.

In particular so-called shell catalysts have proved of value for the production of phthalic anhydride. Here, a support that is inert under the reaction conditions, for example made of quartz (SiO$_2$), porcelain, magnesium oxide, tin dioxide, silicon carbide, rutile, alumina (Al$_2$O$_3$), aluminium silicate, magnesium silicate (steatite), zirconium silicate or cerium silicate, or made of mixtures of the above materials, is used. The support can for example be in the shape of rings, spheres, shells or hollow cylinders. The catalytically active material is applied to it in relatively thin layers (shells). Two or more layers of the same or differently composed catalytically active materials can also be applied.

With respect to the further components of the catalytically active material of the catalyst according to aspects of the invention (in addition to TiO$_2$), reference can be made in principle to the compositions or components described in the relevant state of the art and familiar to a person skilled in the art. These are mainly catalyst systems which, in addition to titanium oxide(s), contain oxides of vanadium. Such catalysts are described e.g. in EP 0 964 744 B1. In many cases, it can be preferred that, for the individual catalyst layers of the catalyst according to aspects of the invention, a V$_2$O$_5$ material with quite small particle size is used in order to promote the application onto the TiO$_2$. For example, at least 90% of the V$_2$O$_5$ particles used can have a diameter of 20 μm or less. Reference can be made here e.g. to DE 103 44 846 A1.

In particular, a range of promoters for increasing the productivity of the catalysts which can also be used in the catalyst according to aspects of the invention is described in the state of the art. These include inter alia the alkali and alkaline-earth metals, thallium, antimony, phosphorus, iron, niobium, cobalt, molybdenum, silver, tungsten, tin, lead and/or bismuth, as well as mixtures of two or more of the above components. According to a preferred embodiment, the catalysts used thus contain one or more of the above promoters. For example, a catalyst is described in DE 21 59 441 A which, in addition to titanium dioxide of the anatase modification, consists of 1 to 30 wt.-% vanadium pentoxide and zirconium dioxide. A list of suitable promoters can also be found in WO 2004/103561, page 5, lines 29 to 37, to which reference is also made. Via the individual promoters, the activity and selectivity of the catalysts can be influenced, in particular by reducing or increasing the activity. The promoters controlling the selectivity include for example the alkali metal oxides and oxidic phosphorus compounds, in particular phosphorus pentoxide.

According to a preferred embodiment, the first catalyst layer, and preferably also the second catalyst layer, contains no phosphorus. It was found that a high activity can thereby be achieved, wherein the selectivity can advantageously be set in the following catalyst layers (3$^{rd}$ and following layer(s)) e.g. by the presence of phosphorus. In some cases, it can be advantageous if only the last layer has phosphorus.

According to a further preferred embodiment, the ratio of vanadium, calculated as V$_2$O$_5$, and antimony, calculated as Sb$_2$O$_3$, in the catalyst of the upstream layer and/or in the catalyst of the 2$^{nd}$ layer is between approximately 3.5:1 and 5:1, as described for example in DE 103 23 461 A.

According to a further preferred embodiment, the alkali metal content, preferably the Cs content, in the catalyst used remains the same or decreases from the 2$^{nd}$ layer to the last layer (at the gas outlet side). In other words:
Cs content of 2$^{nd}$ layer≥Cs content of 3$^{rd}$ layer≥ . . . ≥Cs content of last layer.

Particularly preferably, the last catalyst layer has no Cs.

Numerous suitable methods are described in the state of the art for producing the catalysts according to aspects of the invention. For the production of shell catalysts, reference can be made for example to the method described in DE-A-16 42 938 or DE-A-17 69 998, wherein a solution or suspension containing an aqueous and/or an organic solvent of the components of the catalytically active material and/or its precursor compounds (often called "slurry") is sprayed onto the support material in a heated coating drum at increased temperature, until the desired level of catalytically active material, relative to the total catalyst weight, is achieved. The application (coating) of the catalytically active material onto the inert support can also be carried out in fluidized beds according to DE 21 06 796.

Preferably, so-called shell catalysts are produced by applying a thin layer of the active components of from 50 to 500 μm onto an inert support (e.g. U.S. Pat. No. 2,035,606). In particular spheres or hollow cylinders have proved of value as supports. These shaped bodies result in a high packing density with low loss of pressure and reduce the danger of the formation of packing defects when the catalyst is being poured into the reaction tubes.

The sintered shaped bodies must be heat-proof within the temperature range of the reaction being run. As stated above, for example silicon carbide, steatite, quartz, porcelain, SiO$_2$, Al$_2$O$_3$ or alumina come into consideration.

The advantage of coating support bodies in the fluidized bed is the high uniformity of the layer thickness, which plays a decisive role in the catalytic performance of the catalyst. A particularly uniform coating is obtained by spraying a suspension or solution of the active components onto the heated support at 80 to 200° C. in the fluidized bed, for example according to DE 12 80 756, DE 198 28 583 or DE 197 09 589. Unlike the coating in coating drums, the inside of the hollow cylinders can also be coated uniformly when hollow cylinders are used as supports in the named fluidized bed methods. Of the above-named fluidized bed methods, the method according to DE 197 09 589 in particular is advantageous, as a low abrasion of equipment parts is also achieved, in addition to a uniform coating, by the predominantly horizontal, circular movement of the supports.

For the coating procedure, the aqueous solution or suspension of the active components and an organic binder, preferably a copolymer of vinyl acetate/vinyl laurate, vinyl acetate/ethylene or styrene/acrylate, is sprayed onto the heated, fluidized support via one or more nozzles. It is particularly advantageous to apply the spraying fluid at the site of the highest product speed, whereby the spraying substance can be uniformly distributed in the bed. The spraying procedure is continued until either the suspension is used up or the necessary quantity of active components is applied to the support.

According to a preferred embodiment of the invention, the catalytically active material of the catalyst used is applied in the fluid bed or fluidized bed with the aid of suitable binders, with the result that a shell catalyst is produced. Suitable binders comprise organic binders familiar to a person skilled in the art, preferably copolymers, advantageously in the form of an aqueous dispersion, of vinyl acetate/vinyl laurate, vinyl acetate/acrylate, styrene/acrylate, vinyl acetate/maleate as well as vinyl acetate/ethylene. Particularly preferably, an organic polymer or copolymer adhesive, in particular a vinyl acetate copolymer adhesive, is used as binder. The binder used is added in usual quantities to the catalytically active material, for example at approximately 10 to 20 wt.-%, relative to the solids content of the catalytically active material. For example, reference can be made to EP 744 214. If the catalytically active material is applied at increased temperatures of approximately 150° C., an application onto the support, as known from the state of the art, is also possible without organic binders. Usable coating temperatures when the binders indicated above are used are for example between approximately 50 and 450° C. according to DE 21 06 796. The binders used combust within a short time during the baking of the catalyst in the commissioning of the filled reactor. The binders are primarily used to strengthen the adhesion of the catalytically active material on the support and the reduction in abrasion during transport and when pouring the catalyst in.

Further possible methods for producing shell catalysts for the catalytic gas-phase oxidation of aromatic hydrocarbons to carboxylic acids and/or carboxylic anhydrides have been described for example in EP-A 714 700. According to these, a powder is first produced from a solution and/or a suspension of the catalytically active metal oxides and/or their precursor compounds, optionally in the presence of excipients for catalyst production, and then applied to the support as a shell, optionally after conditioning as well as optionally after heat treatment, to produce the catalytically active metal oxides for the catalyst production and the support coated in this way is subjected to a heat treatment to produce the catalytically active metal oxides or a treatment to remove volatile components.

Suitable conditions for carrying out a method for producing phthalic anhydride from o-xylene and/or naphthalene are equally familiar to a person skilled in the art from the state of the art. In particular, reference is made to the summary description in K. Towae, W. Enke, R. Jäckh, N. Bhargana "Phthalic acid and Derivatives" in Ullmann's Encyclopedia of Industrial Chemistry Vol. A 20, 1992, 181, which is incorporated herein by reference. For example, the boundary conditions known from the above citation WO-A-98/37967 or WO 99/61433 can be chosen for the stationary operating state of the oxidation.

For this, the catalysts are first placed in the reaction tubes of the reactor, which are thermostated from outside to the reaction temperature, for example by means of salt melts. The reaction gas is passed over the thus-prepared catalyst bed at temperatures of generally from 300 to 450° C., preferably 320 to 420° C., and particularly preferably from 340 to 400° C. and at a positive pressure of generally from 0.1 to 2.5, preferably from 0.3 to 1.5 bar absolute, at a space velocity of generally from 750 to 5000 h$^{-1}$.

The reaction gas fed to the catalyst is generally produced by mixing a molecular oxygen-containing gas, which, besides oxygen, can also contain suitable reaction moderators and/or diluents such as steam, carbon dioxide and/or nitrogen, with the aromatic hydrocarbon to be oxidized, wherein the gas containing the molecular oxygen can generally contain 1 to 100, preferably 2 to 50 and particularly preferably 10 to 30 mol.-% oxygen, 0 to 30, preferably 0 to 10 mol.-% water vapour as well as 0 to 50, preferably 0 to 1 mol.-% carbon dioxide, with nitrogen making up the rest. To produce the reaction gas, the gas containing the molecular oxygen is generally charged with 30 to 150 g per Nm$^3$ gas of the aromatic hydrocarbon to be oxidized.

According to a particularly preferred embodiment of the invention, the active material (catalytically active material) of the catalyst of the upstream catalyst layer contains between 5 and 16 wt.-% $V_2O_5$, 0 to 5 wt.-% $Sb_2O_3$, 0.2 to 0.75 wt.-% Cs, 0 to 1 wt.-% P and 0 to 3 wt.-% $Nb_2O_5$. At least 90 wt.-%, preferably at least 95 wt.-%, further preferably at least 98 wt.-%, in particular at least 99 wt.-%, further preferably at least 99.5 wt.-%, in particular 100 wt.-% of the rest of the active material consists of $TiO_2$. According to a particularly preferred embodiment of the invention, the BET surface area of the $TiO_2$ is between 15 and approximately 45 m$^2$/g. Furthermore, it is preferred that such an upstream catalyst layer has a length proportion of 5-25%, particularly preferably 10-25% of the total length of all catalyst layers present (total length of the catalyst bed present).

According to a particularly preferred embodiment of the invention, the active material of the catalyst of the second catalyst layer contains between 5 and 15 wt.-% $V_2O_5$, 0 to 5 wt.-% $Sb_2O_3$, 0.2 to 0.75 wt.-% Cs, 0-1 wt.-% P and 0 to 2 wt.-% $Nb_2O_5$. At least 90 wt.-%, preferably at least 95 wt.-%, further preferably at least 98 wt.-%, in particular at least 99 wt.-%, further preferably at least 99.5 wt.-%, in particular 100 wt.-% of the rest of the active material consists of $TiO_2$. According to a particularly preferred embodiment of the invention, the BET surface area of the $TiO_2$ is between 15 and approximately 25 m$^2$/g. Furthermore, it is preferred that such a second catalyst layer has a length proportion of from approximately 15 to 60%, in particular 20 to 60% or 20 to 50% of the total length of all catalyst layers present (total length of the catalyst bed present).

According to a particularly preferred embodiment, the active material of the catalyst of the third catalyst layer contains 5 to 15 wt.-% $V_2O_5$, 0 to 4 wt.-% $Sb_2O_3$, 0.05 to 0.5 wt.-% Cs, 0 to 1 wt.-% P and 0 to 2 wt.-% $Nb_2O_5$. At least 90 wt.-%, preferably at least 95 wt.-%, further preferably at least 98 wt.-%, in particular at least 99 wt.-%, further preferably at least 99.5 wt.-%, in particular 100 wt.-% of the rest of the active material consists of $TiO_2$. It is preferred that the $TiO_2$ has a BET surface area of between 15 and 25 m$^2$/g. Furthermore, it is preferred that this third layer occupies a length proportion of from approximately 10 to 30% of the total length of all catalyst layers present, in particular if the third layer is the last, thus the layer placed closest to the reactor outlet, a length proportion for the 3$^{rd}$ layer of 20-50% is preferred.

According to a particularly preferred embodiment of the invention, the active material of the catalyst of the fourth catalyst layer contains 5 to 25 wt.-% $V_2O_5$, 0 to 5 wt.-% $Sb_2O_3$, 0 to 0.2 wt.-% Cs, 0 to 2 wt.-% P and 0 to 1 wt.-% $Nb_2O_5$. At least 90 wt.-%, preferably at least 95 wt.-%, further preferably at least 98 wt.-%, in particular at least 99 wt.-%, further preferably at least 99.5 wt.-%, in particular 100 wt.-% of the rest of the active material consists of $TiO_2$. If the fourth layer represents the (last) catalyst layer placed at the gas outlet side of the reactor, a BET surface area of the $TiO_2$ which is somewhat larger than that of the layers placed closer towards the gas inlet side, in particular in the range of between approximately 15 and approximately 45 m$^2$/g, is preferred. Furthermore, it is preferred that such a fourth catalyst layer occupies a length proportion of from approximately 10 to 50%, in particular preferably 10 to 40% of the total length of all catalyst layers present. A fifth catalyst layer is then not necessary as a rule, but is possible.

It was also found that, according to a preferred embodiment, catalysts according to aspects of the invention which have no phosphorus in the catalytically active material in the central and optionally in the upstream (first) catalyst layers preferably make possible good activities with, at the same time, very high selectivity. It is furthermore preferred that at least 0.05 wt.-% of the catalytically active material in the upstream and the central catalyst layers is formed by at least one alkali metal, calculated as alkali metal(s). Caesium is particularly preferred as alkali metal.

The catalysts according to aspects of the invention are usually temperature-treated or calcined (conditioned) before use. It has proved to be advantageous if the catalyst is calcined for at least 24 hours at at least 390° C., in particular for between 24 and 72 hours at ≥400° C., in an $O_2$-containing gas, in particular in air. The temperature preferably should not exceed 500° C., in particular 470° C. In principle, however, other calcining conditions which appear suitable to a person skilled in the art are also not ruled out.

According to a further aspect, the present invention relates to a method for producing a catalyst as described herein, comprising the following steps:
a. providing a catalytically active material as defined herein;
b. providing an inert support, in particular an inert support shaped body;
c. applying the catalytically active material to the inert support, in particular in a fluidized bed or a fluid bed.

The individual catalysts are then placed in the reactor in the desired sequence as catalyst layers, in order to obtain the multilayer catalyst arrangement according to aspects of the invention.

Accordingly, a further aspect of the invention is a method for producing a catalyst arrangement as defined above. The method includes the arrangement of a first catalyst layer of length $L_1$ and at least one second catalyst layer of length $L_2$ each with different catalytic activity with respect to the gas-phase oxidation of hydrocarbons, wherein a catalyst layer K with the length L (L=L1+L2) is formed from the first catalyst layer K1 and the second catalyst layer K2 together and wherein the first catalyst layer is arranged at the gas inlet side for a reaction gas and the second catalyst layer is arranged following the first catalyst layer in the gas flow direction, wherein a catalyst layer with higher catalytic activity than that of the second catalyst layer is used as first catalyst layer.

According to aspects of the invention, it is preferred that the length 0.1 to 0.9 times $A_{HS}$ is chosen as length $L_1$ of the first catalyst layer, wherein $A_{HS}$ means the position of a hotspot (HS) which develops during a gas-phase oxidation of hydrocarbons in a catalyst layer $K_A$, corresponding to the second catalyst layer, with the length L, wherein the position of the hotspot is measured in the gas flow direction from the start at the gas inlet side of the catalyst layer $K_A$ to the hotspot. How the hotspot is determined has already been described in detail above.

The method according to aspects of the invention for producing a catalyst arrangement according to the invention can be carried out either by removing a part of an existing inlet catalyst layer, starting from a starting catalyst arrangement known in the state of the art, and replacing the removed part by a layer with higher activity, or by producing a completely fresh bed corresponding to the catalyst arrangement according to aspects of the invention, wherein the length and/or activity of the first (upstream) catalyst layer is chosen as indicated herein.

For the case where a part of a first catalyst layer $K_A$ of a starting catalyst arrangement is removed and replaced by an upstream catalyst layer, the catalyst layer $K_A$ of the starting catalyst arrangement becomes the second catalyst layer after removal of the desired length proportion. It is preferred that, in the catalyst arrangement according to aspects of the invention, 5 to 60% of the total length of the first catalyst layer and of the second catalyst layer is formed by the first catalyst layer.

As an alternative to removing a part of the catalyst layer $K_A$, a catalyst arrangement can also be formed by using the determined length proportions for an independent catalyst arrangement. In other words, a reactor tube is filled with the necessary quantity of catalyst for the first catalyst layer until the desired length $L_1$ is reached, followed by the second catalyst layer, the length of which corresponds to the length $K_A$ of a starting configuration minus the length $L_1$ of the first catalyst layer. Further layers can be arranged in accordance with the necessary requirements afterwards in the gas flow direction.

Naturally, what was disclosed in detail in the description above applies with respect to the further preferences in relation to the method according to aspects of the invention.

According to a further aspect, the invention also relates to a method for producing phthalic anhydride by gas-phase oxidation of o-xylene and/or naphthalene, wherein a catalyst arrangement, as described above, is used.

Preferably, a catalyst arrangement with three or more layers, as defined in the present description, is used. Generally, a gaseous flow which contains o-xylene and/or naphthalene as well as molecular oxygen is passed over a catalyst arrangement with three or more layers as defined above at increased temperature, in particular between 250 and 490° C.

According to a further aspect, the present invention finally also relates to the use of a catalyst arrangement as defined herein to produce phthalic anhydride by gas-phase oxidation of o-xylene and/or naphthalene.

According to a further aspect, the present invention relates to the use of a first (upstream) catalyst layer to improve a catalyst arrangement having preferably two or more different catalyst layers for the partial oxidation of hydrocarbons, in particular for the production of phthalic anhydride by gas-phase oxidation of o-xylene and/or naphthalene, wherein the activity of the first catalyst layer is higher than the activity of the first catalyst layer of the starting catalyst.

Methods

To determine the parameters of the catalysts used according to aspects of the invention, the following methods are used:

1. Bet Surface Area:

The BET surface area is determined according to the BET method according to DIN 66131; a publication of the BET method is also found in J. Am. Chem. Soc. 60, 309 (1938).

2. Pore Radius Distribution:

The pore radius distribution of the $TiO_2$ used was determined by mercury porosimetry according to DIN 66133; maximum pressure: 2,000 bar, Porosimeter 4000 (Porotec, DE), according to the manufacturer's instructions.

3. Particle Sizes:

The particle sizes were determined according to the laser diffraction method with a Fritsch Particle Sizer Analysette 22 Economy (Fritsch, DE) according to the manufacturer's instructions, including as regards the sample pre-treatment: the sample is homogenized in deionized water without addition of excipients and treated with ultrasound for 5 minutes.

The determination of the BET surface area, the pore radius distribution and the pore volume as well as the particle size distribution took place in respect of the titanium dioxide in each case on the uncalcined material dried under vacuum at 150° C.

The data in the present description with respect to the BET surface areas of the catalysts or catalyst layers also relate to the BET surface areas of the $TiO_2$ material used in each case (dried under vacuum at 150° C., uncalcined, see above).

As a rule, the BET surface area of the catalyst is determined by the BET surface area of the $TiO_2$ used, wherein the BET surface area is altered to a certain extent by adding further catalytically active components. This is familiar to a person skilled in the art.

The active material proportion (proportion of the catalytically active material, without binder) relates in each case to the proportion (in wt.-%) of the catalytically active material in the total weight of the catalyst including support in the respective catalyst layer, measured after conditioning over 4 h at 400° C. in air.

4. Catalyst Activity:

By activity of the catalyst in a catalyst layer is meant according to aspects of the invention the ability of the catalyst to convert the educt used within a defined volume (=control volume), for example a reaction tube of defined length and internal diameter (e.g. 25 mm internal diameter, 1 m length), under predetermined reaction conditions (temperature, pressure, concentration, residence time). Accordingly, the catalyst under consideration has a higher activity than another catalyst if it achieves a higher rate of conversion of educt in this predetermined volume and under the same reaction conditions in each case. In the case of o-xylene or naphthalene as educt, the catalyst activity is thus measured using the level of the conversion of o-xylene or naphthalene to the oxidation products. A higher catalyst activity can be caused either by a nature/quality of the active centres optimized for the desired conversion (cf. for example "turn over frequency") or by an increased number of active centres in the same control volume, which is given for example if more catalyst material with otherwise identical properties is present in the control volume.

Operational Quantification of the Activity:

According to aspects of the invention, the activity of the $1^{st}$ layer is higher than that of the $2^{nd}$ layer. This means, firstly, that—according to the above statement—at the end of a reaction chamber (=reaction tube of defined length and internal diameter, e.g. 25 mm internal diameter, 1 m length) filled with "layer 1 catalyst" and through which the educt mixture flows, there is a higher educt conversion rate than in a comparison experiment carried out in an otherwise identical manner, in which the identical reaction chamber was filled with "layer 2 catalyst".

For such a test, conditions within the following indicated ranges are expediently chosen:
length of reaction tube: 1 m
internal diameter of reaction tube: 25 mm
temperature of cooling medium: 380-420° C.
pressure: 1-1.5 bar absolute
o-xylene charge of educt mixture: 60 g o-xylene/$Nm^3$ air The quantification of the activity of the first catalyst layer compared with the activity of the second catalyst layer can then be determined as follows using the following definition according to the invention of a "catalyst with 10% higher activity" used for layer 1 compared with a catalyst used for layer 2:

The educt mixture flows through the comparison catalyst (=layer 2 catalyst with the envisaged composition) under the conditions indicated above, wherein the total volumetric flow through the reaction tube is set such that the o-xylene conversion rate after flowing through the reaction chamber is as close as possible to 50%.

In a second experiment, the same reaction volume is filled with layer 1 (test) catalyst, which differs from layer 2 catalyst only in that the proportion of the catalytically active material (active material proportion) is 10% higher. Thus, there is 10% more active material in the reaction volume than in the case of the comparison catalyst arrangement. The o-xylene conversion rate after flowing through the reaction chamber filled with layer 1 catalyst is then determined under the same reaction conditions. This is higher than with the comparison catalyst, thus higher than 50%. The difference between the thus-obtained o-xylene conversion rate and the 50% conversion rate of the comparison catalyst is used as a relative measure which corresponds to a 10% increase in activity. It is unimportant which change to the catalyst achieves such an effect. Accordingly, e.g. with a catalyst which differs from the envisaged layer 2 catalyst only in that the active material proportion is 20% higher, a measure for a 20% increased activity of the catalyst can be determined, etc.

The maximum measured temperature in the whole catalyst bed is called hotspot in the above description. Furthermore, there are also (secondary) hotspots, i.e. maximum temperatures, in each case in the further catalyst layers under consideration. The temperature is preferably measured via thermocouples.

The invention will now be described in more detail with the help of the following examples which are not to be considered as limiting the scope of the invention:

EMBODIMENT EXAMPLES

Example 1

Starting Catalyst

As starting catalyst, a 3-layer catalyst arrangement with the following composition and layer length is placed in a tube reactor cooled with a salt bath and having an internal diameter of 25 mm. A 3-mm thermowell with incorporated movable element for temperature measurement was located, centrally arranged, in the reaction tube. 4 $Nm^3$ air with a charge of 30-100 g o-xylene/$Nm^3$ air (purity o-xylene>99%) was passed through the tube hourly from top to bottom at a total pressure of approximately 1450 mbar.

At a charge of 60-65 g o-xylene/$Nm^3$ air, the hotspot in the first layer was measured at a position of 90-100 cm (from the start of the bed towards the reactor outlet) at salt bath temperatures of between 370 and 375° C.

| Composition | Layer 1 length: 150 cm | Layer 2 length: 60 cm | Layer 3 length: 80 cm |
|---|---|---|---|
| $V_2O_5$/wt.-% | 7.5 | 7.5 | 7.5 |
| $Sb_2O_3$/wt.-% | 3.2 | 3.2 | 3.2 |
| Cs/wt.-% | 0.4 | 0.2 | 0.1 |
| P/wt.-% | 0.2 | 0.2 | 0.2 |
| $TiO_2$/wt.-% | remainder to 100% | remainder to 100% | remainder to 100% |
| BET $TiO_2$/wt.-% | 20 | 20 | 30 |
| Proportion AM/wt.-% | 8.0 | 7.5 | 7.5 |

Catalyst Arrangement According to Aspects of the Invention

On the basis of the results obtained with the starting catalyst configuration for the positioning of the hotspot (A=90 to 100 cm), a catalyst arrangement according to aspects of the invention was now produced as follows:

The above composition of the 3-layer starting catalyst arrangement was modified to the extent that 50 cm of layer 1 of the starting catalyst arrangement (from the gas inlet side or start of the catalyst bed) was replaced by a more active upstream catalyst layer. The composition and layer length of the improved 4-layer catalyst system according to aspects of the invention can be seen from the following table. Layer 1 corresponds to the upstream catalyst layer according to the invention (first catalyst layer); the composition of layer 2 corresponds (except for the layer length) to that of layer 1 of the starting catalyst arrangement. The composition and layer length of layers 3 and 4 correspond to those of layers 2 and 3 of the starting catalyst arrangement. The 4-layer catalyst arrangement according to the invention with the following composition and layer length was placed in a tube reactor cooled with a salt bath and having an internal diameter of 25 mm. A 3-mm thermowell with incorporated movable element for temperature measurement was located, centrally arranged, in the reaction tube. 4 $Nm^3$ air with a charge of 30-100 g o-xylene/$Nm^3$ air (purity o-xylene>99%) was passed through the tube hourly from top to bottom at a total pressure of approximately 1450 mbar.

At a charge of 60-65 g o-xylene/$Nm^3$ air, the hotspot under consideration above was measured at a position of 75-85 cm (from the start of the bed towards the reactor outlet) at salt bath temperatures of between 365 and 375° C.

| Composition | Layer 1 length: 50 cm | Layer 2 length: 100 cm | Layer 3 length: 60 cm | Layer 4: length: 80 cm |
|---|---|---|---|---|
| $V_2O_5$/wt.-% | 8.0 | 7.5 | 7.5 | 7.5 |
| $Sb_2O_3$/wt.-% | 3.2 | 3.2 | 3.2 | 3.2 |
| Cs/wt.-% | 0.4 | 0.4 | 0.2 | 0.1 |
| P/wt.-% | 0.2 | 0.2 | 0.2 | 0.2 |
| $TiO_2$/wt.-% | remainder to 100% | remainder to 100% | remainder to 100% | remainder to 100% |
| BET $TiO_2$/($m^2$/g) | 20 | 20 | 20 | 30 |
| Proportion AM/wt.-% | 10 | 8 | 7.5 | 7.5 |

The position of the hotspot in the example according to aspects of the invention is thus significantly closer to the reactor inlet than in the comparison example.

The following advantages can be derived from this for the catalyst arrangement according to aspects of the invention, which apply not only to the specific example, but to the present invention in general:
- longer life, as the hotspot at the start of the reaction and therefore also during continuing deactivation is closer to the reactor inlet, in particular remains in the $2^{nd}$ layer (formerly $1^{st}$ layer) for longer.
- lower level of maleic anhydride, phthalide and other by-products in the reaction gas which leaves the reactor as the reaction is shifted further towards the front.
- the (secondary) hotspot in the $3^{rd}$ layer is lower than with the starting catalyst arrangement in the equivalent $2^{nd}$ layer, as more o-xylene is converted in the two previous layers 1 and 2 than in the starting catalyst arrangement in layer 1.

The invention claimed is:

1. A method for producing/optimizing a catalyst arrangement for the gas-phase oxidation of hydrocarbons comprising the arrangement of a first catalyst layer of length $L_1$ and at least one second catalyst layer of length $L_2$, each with different catalytic activities with respect to the gas-phase oxidation of hydrocarbons, wherein the first catalyst layer is arranged at the gas inlet side for a reaction gas and the at least one second catalyst layer is arranged following the first catalyst layer in the gas flow direction, wherein the catalyst arrangement has a temperature profile during the gas-phase oxidation of hydrocarbons which increases from the first catalyst layer to the second.

2. The method according to claim 1, wherein a catalyst layer with higher catalytic activity than that of the second catalyst layer is used as first catalyst layer.

3. The method according to claim 1, wherein the temperature profile is such that during the gas-phase oxidation of hydrocarbons the maximum temperature in the first catalyst layer is 10 to 100° C. lower than in the second catalyst layer.

4. The method according to claim 1, wherein the value 0.1 to 0.9 times $A_{HS}$ is chosen as length $L_1$ for the first catalyst layer, wherein $A_{HS}$ means the position of a temperature maximum (hotspot) which develops during a gas-phase oxidation of hydrocarbons in a catalyst layer $K_A$, corresponding to the second catalyst layer, with the total length $L=L_1+L_2$, wherein the position of the temperature maximum is measured in the gas flow direction from the start of the catalyst layer $K_A$ at the gas inlet side to the hotspot.

5. The method according to claim 1, wherein a third catalyst layer is arranged after the second catalyst layer in the gas flow direction, wherein the catalytic activity increases from the second catalyst layer to the third catalyst layer.

6. The method according to claim 5, wherein the temperature profile decreases from the second catalyst layer to the third.

7. The method according to claim 5, wherein the temperature profile is such that during the gas-phase oxidation of hydrocarbons the maximum temperature in the third catalyst layer is 10 to 100° C. lower than in the second catalyst layer.

8. The method according to claim 5, wherein a fourth catalyst layer is arranged after the third catalyst layer in the gas flow direction, wherein the catalytic activity increases from the third catalyst layer to the fourth catalyst layer.

9. The method according to claim 8, wherein the temperature profile decreases from the second catalyst layer to the fourth.

10. The method according to claim 8, wherein the temperature profile is such that during the gas-phase oxidation of hydrocarbons the maximum temperature in the fourth catalyst layer is 10 to 100° C. lower than in the second and/or third catalyst layer.

11. The method according to claim 1, wherein the range smaller than or equal to 0.9 is chosen as ratio of the length of the first catalyst layer to the second catalyst layer.

12. The method according to claim 1, wherein approximately 5 to 60% of the total length of the first and second catalyst layers is formed from the first catalyst layer.

13. The method according to claim 1, wherein the length of the first catalyst layer is approximately 5 to 30% of the length of all catalyst layers, relative to the total length of the catalyst arrangement in the gas flow direction.

14. The method according to claim 1, wherein the different catalytic activity in the respective catalyst layers is set by different chemical and/or physical properties of the catalysts contained in the respective catalyst layers.

15. The method according to claim 1, wherein the catalysts used in the catalyst layers have an inert support and a catalytically active material arranged thereon.

16. The method according to claim 15, wherein the catalytically active material comprises a titanium-containing support oxide and a catalytically active composition.

17. The method according to claim 16, wherein the titanium-containing support oxide has a BET surface area of from 10 to 50 m²/g.

18. The method according to claim 15, wherein the catalytically active material comprises vanadium, niobium, antimony, boron, calcium, caesium, potassium, lithium, sodium, cobalt, iron, molybdenum, zirconium, rubidium, silver, thallium, bismuth, tungsten, tin, phosphorus and/or compounds and/or combinations thereof.

19. The method according to claim 15, wherein the proportion of the catalytically active material is 4 to 20 wt.-%, relative to the total weight of the catalyst.

20. A method for producing phthalic anhydride by catalytic gas-phase oxidation of o-xylene and/or naphthalene, wherein the method is carried out by means of a catalyst arrangement which has a first catalyst layer at the gas inlet side and at least one second catalyst layer after the first catalyst layer in the gas flow direction with different catalytic activities, wherein when the gas-phase oxidation is being carried out a lower maximum temperature (hotspot temperature) is formed in the first catalyst layer than in the second catalyst layer.

21. The method according to claim 20, wherein a maximum temperature is formed in the first catalyst layer that is 10 to 100° C. lower than in the second catalyst layer.

22. The method according to claim 20, wherein the catalytic activity of the first catalyst layer is higher than that of the second catalyst layer.

23. The method according to claim 20, wherein the catalyst arrangement used has a third catalyst layer which is arranged after the second catalyst layer in the gas flow direction, wherein the catalytic activity increases from the second catalyst layer to the third catalyst layer.

24. The method according to claim 23, wherein a maximum temperature is formed in the third catalyst layer that is 10 to 100° C. lower than in the second catalyst layer.

25. The method according to claim 23, wherein the catalyst arrangement used has a fourth catalyst layer which is arranged after the third catalyst layer in the gas flow direction and wherein the catalytic activity increases from the third catalyst layer to the fourth catalyst layer.

26. The method according to claim 25, wherein a maximum temperature is formed in the fourth catalyst layer that is 10 to 100° C. lower than in the second and/or third catalyst layer.

27. The method according to claim 20, wherein the range smaller than or equal to 0.9 is chosen as ratio of the length of the first catalyst layer to the second catalyst layer.

28. The method according to claim 20, wherein approximately 5 to 60% of the total length of the first and second catalyst layers consists of the first catalyst layer.

29. The method according to claim 20 wherein the length of the first catalyst layer is approximately 5 to 30% of the length of all catalyst layers, relative to the total length of the catalyst arrangement in the gas flow direction.

30. The method according to claim 20, wherein the different catalytic activity in the respective catalyst layers is set by different chemical and/or physical properties of the catalysts contained in the respective catalyst layers.

31. The method according to claim 20, wherein the catalysts used in the catalyst layers have an inert support and a catalytically active material arranged thereon.

32. The method according to claim 20, wherein the catalytically active material comprises a titanium-containing support oxide and a catalytically active composition.

33. The method according to claim 32, wherein the titanium-containing support oxide has a BET surface area of from 10 to 50 m²/g.

34. The method according to claim 32, wherein the catalytically active material comprises vanadium, niobium, antimony, boron, calcium, caesium, potassium, lithium, sodium, cobalt, iron, molybdenum, zirconium, rubidium, silver, thallium, bismuth, tungsten, tin, phosphorus and/or compounds and/or combinations thereof.

35. The method according to claim 32, wherein the proportion of the catalytically active material is 4 to 20 wt.-%, relative to the total weight of the catalyst.

36. A catalyst comprising a first catalyst layer $K_1$ of length $L_1$ and at least one second catalyst layer $K_2$ of length $L_2$, each with different catalytic activities with respect to the gas-phase oxidation of hydrocarbons, wherein the first catalyst layer $K_1$ and the at least one second catalyst layer $K_2$ together form a catalyst layer K with the total length $L_1+L_2$ and wherein the first catalyst layer $K_1$ is arranged at the gas inlet side for a reaction gas and the second catalyst layer $K_2$ is arranged after the first catalyst layer $K_1$ in the gas flow direction, wherein the catalyst has a temperature profile which increases during the gas-phase oxidation of hydrocarbons from the first catalyst layer to the second.

37. The catalyst according to claim 36, wherein the catalytic activity of the first catalyst layer is higher than that of the second catalyst layer.

38. The catalyst according to claim 36, wherein the temperature profile is such that the maximum temperature during the gas-phase oxidation of hydrocarbons in the first catalyst layer is 10 to 100° C. lower than in the second catalyst layer.

39. The catalyst according to claim 36, wherein the length $L_1$ for the first catalyst layer is 0.1 to 0.9 times $A_{HS}$, wherein $A_{HS}$ means the position of a temperature maximum (hotspot) which develops during a gas-phase oxidation of hydrocarbons in a catalyst layer $K_A$, corresponding to the second catalyst layer, of a starting catalyst arrangement with the total length $L=L_1+L_2$, wherein the position of the temperature maximum is measured in the gas flow direction from the start of the catalyst layer $K_A$ at the gas inlet side to the hotspot.

40. The catalyst according to claim 36, wherein a third catalyst layer is arranged after the second catalyst layer in the gas flow direction, wherein the catalytic activity increases from the second catalyst layer to the third catalyst layer.

41. The catalyst according to claim 40, wherein the temperature profile decreases from the second catalyst layer to the third.

42. The catalyst according to claim 40, wherein the temperature profile is such that the maximum temperature during the gas-phase oxidation of hydrocarbons in the third catalyst layer is 10 to 100° C. lower than in the second catalyst layer.

43. The catalyst according to claim 40, wherein a fourth catalyst layer is arranged after the third catalyst layer in the gas flow direction, wherein the catalytic activity increases from the third catalyst layer to the fourth catalyst layer.

44. the catalyst according to claim 43, wherein the temperature profile decreases from the second catalyst layer to the fourth.

45. The catalyst according to claim 43, wherein the temperature profile is such that the maximum temperature during the gas-phase oxidation of hydrocarbons in the fourth catalyst layer is 10 to 100° C. lower than in the second and/or third catalyst layer.

46. The catalyst according to claim 36, wherein the ratio of the length of the first catalyst layer to the second catalyst layer is smaller than or equal to 0.9.

47. The catalyst according to claim 36, wherein approximately 5 to 60% of the total length of the first and second catalyst layers consists of the first catalyst layer.

48. The catalyst according to claim 36, wherein the length of the first catalyst layer is approximately 5 to 30% of the length of all catalyst layers, relative to the total length of the catalyst in the gas flow direction.

49. The catalyst according to claim 36, wherein the different catalytic activity in the respective catalyst layers is conditional on different chemical and/or physical properties of the catalysts contained in the respective catalyst layers.

50. The catalyst according to claim 36, wherein the catalysts used in the catalyst layers have an inert support and a catalytically active material arranged thereon.

51. The catalyst according to claim 50, wherein the catalytically active material comprises a titanium-containing support oxide and a catalytically active composition.

52. The catalyst according to claim 51, wherein the titanium-containing support oxide has a BET surface area of from 10 to 50 $m^2/g$.

53. The catalyst according to claim 50, wherein the catalytically active material comprises vanadium, niobium, antimony, boron, calcium, caesium, potassium, lithium, sodium, cobalt, iron, molybdenum, zirconium, rubidium, silver, thallium, bismuth, tungsten, tin, phosphorus and/or compounds and/or combinations thereof.

54. The catalyst according to claim 50, wherein the proportion of the catalytically active material is 4 to 20 wt.-%, relative to the total weight of the catalyst.

* * * * *